US011769581B2

(12) United States Patent
Houston et al.

(10) Patent No.: US 11,769,581 B2
(45) Date of Patent: Sep. 26, 2023

(54) SYSTEM AND METHOD FOR CLINICAL ASSESSMENTS AND INTERVENTIONS USING MULTIDIMENSIONAL SCALING ANALYSIS

(71) Applicant: CHARLES R. DREW UNIVERSITY OF MEDICINE AND SCIENCE, Los Angeles, CA (US)

(72) Inventors: Eric Houston, Los Angeles, CA (US); Sukrit Mukherjee, Los Angeles, CA (US)

(73) Assignee: CHARLES R. DREW UNIVERSITY OF MEDICINE AND SCIENCE, Los Angeles, CA (US)

( * ) Notice: Subject to any disclaimer, the term of this patent is extended or adjusted under 35 U.S.C. 154(b) by 355 days.

(21) Appl. No.: 16/865,131

(22) Filed: May 1, 2020

(65) Prior Publication Data

US 2020/0365251 A1      Nov. 19, 2020

Related U.S. Application Data

(60) Provisional application No. 62/848,954, filed on May 16, 2019.

(51) Int. Cl.
| | |
|---|---|
| G16H 20/70 | (2018.01) |
| G16H 50/50 | (2018.01) |
| G16H 40/63 | (2018.01) |
| G16H 50/20 | (2018.01) |
| G16H 10/60 | (2018.01) |
| G16H 50/30 | (2018.01) |
| G16H 15/00 | (2018.01) |

(52) U.S. Cl.
CPC .............. *G16H 20/70* (2018.01); *G16H 10/60* (2018.01); *G16H 15/00* (2018.01); *G16H 40/63* (2018.01); *G16H 50/20* (2018.01); *G16H 50/30* (2018.01); *G16H 50/50* (2018.01)

(58) Field of Classification Search
CPC ........ G16H 20/70; G16H 10/60; G16H 15/00; G16H 40/63; G16H 50/20; G16H 50/30; G16H 50/50
See application file for complete search history.

(56) References Cited

U.S. PATENT DOCUMENTS 9,302,179 B1 * 4/2016 Merzenich ............... G09B 5/00

OTHER PUBLICATIONS

Teresa A. Treat, et al., "Assessing Clinically Relevant Perceptual Organization With Multidimensional Scaling Techniques" Psychological Assessment vol. 14, No. 3, p. 239-252 (c) 2002 (Year: 2002).*

(Continued)

*Primary Examiner* — Gregory D. Moseley
(74) *Attorney, Agent, or Firm* — PILLSBURY WINTHROP SHAW PITTMAN LLP (57) ABSTRACT

Given longstanding problems with patient engagement across the continuum of care and the need to address growing health disparities, individualized assessments represent an important element in clinical interventions. The present method (and system that executes this method) is a novel procedure that employs idiographic techniques, an n-tier cross-platform architecture, and system features that automatically and quickly generate individualized patient assessment data for use in clinical interventions.

9 Claims, 5 Drawing Sheets

(56) References Cited

OTHER PUBLICATIONS

Aday, Jacob Scott, "Evaluating the Use of Self-Relevant Stimuli in Attention Bias Modification Training as a Treatment for Anxiety: A Near-Infrared Spectroscopy Study" (2017). All NMU Master's Theses. 145. https://commons.nmu.edu/theses/145 (Year: 2017).*

* cited by examiner

SYSTEM AND METHOD FOR CLINICAL ASSESSMENTS AND INTERVENTIONS USING MULTIDIMENSIONAL SCALING ANALYSIS

BACKGROUND

1. Field

The present disclosure relates generally to clinical assessments and interventions using multidimensional scaling analysis.

2. Description of the Related Art

In mental health and substance abuse treatment, individualized assessments provide information on the specific thoughts and cognitive processes that influence a person's behaviors, emotional responses, and psychological functioning. Having information about the individual's thoughts and cognitive processes facilitates the development of clinical interventions tailored specifically to an individual patient. Research suggests that interventions based on information from such individualized assessments are likely to have greater effectiveness than those that do not. Interventions that incorporate these individual-specific thoughts and cognitive processes are likely to resonate more strongly with patients than interventions lacking this focus. In addition, using individualized assessments to inform and implement treatment also heightens patient motivation and may strengthen efforts to promote their retention in treatment.

SUMMARY

The following is a non-exhaustive listing of some aspects of the present techniques. These and other aspects are described in the following disclosure.

Some aspects include an automated method for clinical assessments and interventions using multidimensional scaling analysis. The method comprises receiving, with an N-tier computer software system, input information comprising paired comparisons ratings from a user. The method comprises transforming, with the computer software system, the input information into a data matrix. The method comprises generating, with the computer software system, using multidimensional scaling analysis based on the data matrix, an N-dimensional spatial configuration or mapping that indicates stress values, a least distance value, and/or R-values for the user. The method comprises causing, with the computer software system, display of the N-dimensional spatial configuration or mapping.

Some aspects include a tangible, non-transitory, machine-readable medium storing instructions that when executed by a data processing apparatus cause the data processing apparatus to perform operations including the above-mentioned process.

Some aspects include a system, including: one or more processors; and memory storing instructions that when executed by the processors cause the processors to effectuate operations of the above-mentioned process.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the description below and the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of mental health and substance abuse treatment. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Given longstanding problems with patient engagement across the continuum of care and the need to address growing health disparities, individualized assessments represent an important element in clinical interventions. The present method (and system that executes this method) is a novel procedure that employs idiographic techniques, an n-tier cross-platform architecture, and system features that automatically and quickly generate individualized patient assessment data for use in clinical interventions.

Idiographic Assessment Approaches

Paired comparisons techniques and multidimensional scaling (MDS) analyses are two data analytic techniques that have traditionally been used in statistics and research. In the present system and method, however, the two data analytic techniques are presented as part of a novel approach in the delivery of care to individuals enrolled in behavioral health interventions. The present system and method involve the novel use of these techniques in a unique software system designed to automatically provide individualized assessments for immediate use in clinical interventions. Such assessments could be used to deliver treatment to hard-to-reach or poorly engaged patients. Existing software does not provide output from these analytic techniques to provide assessments in an immediate and automated manner. The present software system includes these capabilities, which are often needed in clinical settings.

In paired comparisons techniques, individuals rate the similarity or dissimilarity of two different items based on their own personal criteria. In the present idiographic assessment program, the items that individual patients rate include their own thoughts, perceptions, and beliefs. These items are elicited during a brief interview task that would precede ratings by the patient. The patient ratings would subsequently be subjected to MDS analyses, using a unique and specialized algorithm that examines the data and automatically generates a spatial mapping for a visual depiction of the underlying structure of how an individual patient's thoughts and cognitive processes influence their behaviors, emotions, and psychological functioning.

To date, paired-comparisons techniques and MDS have not been combined for use, in neither automated assessment procedures, nor individualized clinical interventions. The novel use of such idiographic approaches may be particularly valuable in clinical settings that lack staff trained in clinical interviewing or individualized assessment techniques. Thus, the method is likely to have strong market potential. The customer base for such an assessment procedure would include hospitals, clinics and substance use treatment centers as well as private practitioners and agencies and organizations involved in health care delivery in the United States and abroad.

Summary of the Methods

The combined use of paired-comparisons techniques and MDS through automated, cross-platform processes allows for the collection of important information from patients. The gathering of such information often requires intensive, time-consuming interviews, but the present idiographic assessment system and method uniquely allow for this information to be obtained and processed with significantly less time and then subsequently available for immediate use in a range of clinical interventions and approaches, including those involving attention bias modification training, cognitive mapping techniques, and motivational interviewing. The automated nature of the present assessment approach and the relative speed with which the information can be applied is novel and has much potential in addressing gaps in the delivery of care. The following section describes how the present idiographic assessment system and method may be used in clinical interventions, such as those employing attention bias modification (ABM), cognitive mapping, and motivation intervention.

Attention Bias Modification (ABM)

ABM is a treatment approach delivered via computer. ABM aims to reduce symptoms of depressive and anxiety disorders, and it has been used to increase health-promoting behaviors by modifying an individual's attentional biases. In a ABM training, individuals are presented with a modified dot-probe task in which they are initially asked to view a computer screen and watch a fixation cross situated in the center of the screen. Two stimuli (e.g., words, images, or faces that have contrasting combinations of either negative, positive, or neutral connotations) replace the cross, appearing simultaneously on opposite sides of the screen for a very brief duration (e.g., 2 secs or less). Then, a dot appears on the screen in the location of one of the previous stimuli. At this time, participants must indicate the location of the dot as quickly as possible. In ABM, the dot appears in the location of neutral or positive stimuli nearly always (e.g., 90% of the time), thereby training participants to learn to respond more quickly to these types of stimuli with shorter reaction times instead of the negative stimuli which have greater salience to them due to depressive symptoms. With repeated trials, the attentional bias toward negative stimuli is reduced and participants learn to redirect or retrain their attentional focus toward neutral or positive stimuli.

Previous ABM trainings have used generic stimuli to induce changes in symptoms or behaviors. The present assessment system and method, however, introduces a novel adaptation of ABM that would allow for individualized ABM training. The individualized training uses stimuli that reflect a patient's salient thoughts, beliefs, and cognitive processes that may underlie a given psychological or health problem. Research suggests that this type of personally meaningful stimuli may have greater impact on long-term behavior change because it taps into both explicit and implicit cognitive processes.

Stimuli for the individualized ABM training are derived from the present idiographic assessment procedure, which as described, is based on paired-comparisons techniques and multidimensional scaling analysis. The approach represents an innovative process for obtaining stimuli to be used in ABM and conducting subsequent ABM training interventions. Existing ABM trainings do not feature stimuli derived from idiographic assessments. These trainings tend to use a modified dot probe task with stimuli consisting primarily of pictures or words. In addition, existing ABM trainings are not generally individualized and do not include stimuli designed to tap both explicit and implicit cognitive processes. Published research suggests that filling these gaps in the scientific literature base may have a substantial impact on treatment outcomes and patient retention. The present assessment procedure may have important applications and address a range of clinical issues and health disparities.

The present system and method may facilitate the development of ABM trainings that are tailored to the individual based on his or her own personally meaningful stimuli (i.e., thoughts, beliefs, cognitive processes). Thoughts vary from individual to individual with regard to their salience in influencing treatment behaviors and symptoms of psychological distress. For example, some thoughts are strongly connected to negative mood and treatment avoidance while others are positively valenced and associated with treatment engagement. To make sure the attention of an individual is reoriented away from his own thoughts that are dysphoric and treatment avoidant and toward those that are positively valenced and associated with treatment approach behaviors, the present system and method includes the administration of an individualized, multidimensional assessment to individual participants. Research indicates that idiographic stimuli have stronger attentional biases than general stimuli. The multidimensional assessment can be used to identify the appropriate treatment-related thoughts and cognitive processes for use as stimuli in the individualized ABM training.

The multidimensional assessment technique is a novel approach that serves as the basis for the idiographic ABM procedure. Databases, including Pubmed and PsychInfo, show no evidence of inventions designed to provide idiographic stimuli for ABM trainings. The present assessment process is fully automated and the stimuli generated by the present system can be assessed via the web, thereby addressing issues related to patient engagement and health disparities.

Cognitive Mapping

Cognitive maps are used in connection with a variety of interventions, including those designed to promote substance abuse treatment, emotion regulation, and condom use. Cognitive maps, which provide a graphic depiction of an individual's thought processes, may be used as part of interventions that provide clients with a visual aid for adaptive regulation of behavior. By graphically depicting cognitive processes and behaviors, cognitive maps are designed to facilitate patient awareness of alternative, health-promoting behaviors that they could follow when tempted by negative behaviors. Cognitive maps are traditionally generated manually and often on the spot. The present system and method, however, use both explicit and implicit cognitive processes and obtain information indirectly and in a manner that addresses the problem of response bias. Thus, the development of cognitive maps using the present idiographic automated techniques is more likely to produce maps that more fully capture an individual's thought processes than existing cognitive mapping techniques.

The use of multidimensional analysis and paired-comparisons is novel approach in the development of cognitive maps. In addition, cognitive maps developed through the present method may be used to address health disparities because of their readily available access through laptops and mobile devices in a variety of both clinical and community settings based on patient needs.

Motivational Interviewing

Using the present idiographic assessment approach, individuals are asked to articulate a wide range of thoughts they hold that describe behaviors related to treatment or the clinical issue (e.g., depression, anxiety, poor treatment adherence). Individuals are then asked to rate the similarity of these thoughts to one another and their treatment-related behavior using a computer-based program. The program presents possible pairings of the patient's treatment-related thoughts in random order on the computer screen, in quick succession. Using a 7-point (for example) rating scale, participants are asked to enter similarity ratings as a pairing appears on the screen. These similarity ratings are subsequently examined by the present system and method using multidimensional scaling analysis (MDS). Based on the similarity ratings, MDS generates mappings that depict the relationship of the thoughts and cognitive processes to an individual's treatment avoidance or engagement behavior. Many individuals experiencing depressive symptoms are unaware of how their thought processes are connected to their treatment behaviors, and they have difficulty accessing adaptive thoughts during times of escalating depressive symptoms. MDS allows for the identification of these implicit cognitive processes as either being related to treatment avoidance or treatment engagement as well as the extent to which they may be positively-valenced or negatively-valenced for the individual, and thus connected to changes in mood.

In the present system and method, MDS may be used to facilitate an individualized assessment that provides immediate information about the patient's treatment-related cognitive processes. This information may not otherwise be readily obtainable without the use of the specialized interviewing techniques of the present system and method, such as Motivational Interviewing. Many healthcare professionals lack training in Motivational Interviewing or work in settings where they face staffing demands that prevent them from engaging in these interviewing approaches. The present assessment approach may address a gap in professional training and staff resources. The present approach is automated and web-based, thereby addressing issues related patient access and engagement.

Example illustrations of at least some of the functionality described above are included in FIG. 1-4 included below.

Example System Components

The following paragraphs describe one or more components that may be included in the present system and/or may execute one or more of the method operations described herein.

In the some embodiments, the system may include and/or the method may include operations executed by, one or more of the computers described below with reference to FIG. 5. Such computers may be and/or include an application program interface (API) server, a web server, a data store, a cache server, and/or other computing systems. These components, in some embodiments, communicate with one another in order to provide the functionality described herein. In some embodiments, the data store may store data about users (e.g., user information), user interaction with the system, assessments related to users, or other information. The cache server may expedite access to this data by storing likely relevant data in relatively high-speed memory, for example, in random-access memory or a solid-state drive. The web server may serve webpages having graphical user interfaces that display various views associated with the system. The API server may serve data to various applications that process data related to operations of the present system and method. The operation of these components may be coordinated by one or more controllers or other components, which may bidirectionally communicate with each of these components or direct the components to communicate with one another. Communication may occur by transmitting data between separate computing devices (e.g., via transmission control protocol/internet protocol (TCP/IP) communication over a network), by transmitting data between separate applications or processes on one computing device; or by passing values to and from functions, modules, or objects within an application or process, e.g., by reference or by value.

Among other operations, the present method (and system) may include linking login information to previously stored user profile information for a user. In some embodiments, this and other interactions with users may occur via a website or a native application viewed on a desktop computer, tablet, or a laptop of the user. In some cases, such interaction occurs via a mobile website viewed on a smart phone, tablet, or other mobile user device, or via a special-purpose native application executing on a smart phone, tablet, or other mobile user device. Facilitating interactions across a variety of devices is expected to make it easier for the user to provide information and/or otherwise use the system and method described herein when and where convenient for the user.

The system may include and/or the method may operate on mobile user devices; desk-top user devices; various servers, external resources, or other components. These devices may communicate via a network, such as the Internet or the Internet in combination with various other networks, like local area networks, cellular networks, or personal area networks.

The mobile user devices may be smart phones, tablets, gaming devices, or other hand-held networked computing devices having a display, a user input device (e.g., buttons, keys, voice recognition, or a single or multi-touch touch-screen), memory (such as a tangible, machine-readable, non-transitory memory), a network interface, a portable energy source (e.g., a battery), and a processor (a term which, as used herein, includes one or more processors) coupled to each of these components. The memory of the mobile user devices may store instructions that when executed by the associated processor provide an operating system and various applications, including a web browser or a native mobile application. The desk-top user devices may also include a web browser. In addition, the desktop user devices may include a monitor; a keyboard; a mouse; memory; a processor; and a tangible, non-transitory, machine-readable memory storing instructions that when executed by the processor provide an operating system and the web browser. Native applications and the web browsers, in some embodiments, are operative to provide a graphical user interface associated with the system that facilitates user interaction with the system. The web browsers may be configured to receive a website from one or more other components of the present system having data related to instructions (for example, instructions expressed in JavaScript™) that when executed by the browser (which is executed by the processor) cause the mobile user devices and/or the desktop user devices to facilitate user interaction with the system. The native applications and the web browsers, upon rendering a webpage and/or a graphical user interface, may generally be referred to as client applications of a system server. Embodiments, however, are not limited to client/server architectures, and the present system may include a variety of components other than those functioning primarily as a server.

External resources, in some embodiments, include sources of information such as databases, websites, etc.; external entities participating with the present system (e.g., systems or networks associated with health care providers), one or more servers outside of the present system, a network (e.g., the internet), electronic storage, equipment related to Wi-Fi™ technology, equipment related to Bluetooth® technology, data entry devices, or other resources. In some implementations, some or all of the functionality attributed herein to external resources may be provided by resources included in the present system. External resources may be configured to communicate with other components of the system via wired and/or wireless connections, via a network (e.g., a local area network and/or the internet), via cellular technology, via Wi-Fi technology, and/or via other resources.

Various components of the present system may be configured to communicate via a protocol, such as a representational-state-transfer (REST)-based API protocol over hypertext transfer protocol (HTTP) or other protocols. API requests may identify which data is to be displayed, linked, modified, added, or retrieved by specifying criteria for identifying records, such as queries for retrieving or processing information about a particular user, for example.

A web or other server of the present system may be configured to display, link, modify, add, or retrieve portions or all of various information encoded in a webpage (e.g. a collection of resources to be rendered by the browser and associated plug-ins, including execution of scripts, such as JavaScript™, invoked by the webpage). In some embodiments, the graphical user interface presented by the webpage may include inputs by which the user may enter or select data, such as clickable or touchable display regions or display regions for text input. Such inputs may prompt the browser to request additional data from the web server or transmit data to the web server, and the web server may respond to such requests by obtaining the requested data and returning it to the user device or acting upon the transmitted data (e.g., storing posted data or executing posted commands). In some embodiments, the requests are for a new webpage or for data upon which client-side scripts will base changes in the webpage, such as XMLHttpRequest requests for data in a serialized format, e.g. JavaScript™ object notation (JSON) or extensible markup language (XML). The web server may communicate with web browsers, such as the web browsers executed by user devices. In some embodiments, a webpage is modified by the web server based on the type of user device, e.g., with a mobile webpage having fewer and smaller images and a narrower width being presented to the mobile user device, and a larger, more content rich webpage being presented to the a desk-top user device. An identifier of the type of user device, either mobile or non-mobile, for example, may be encoded in the request for the webpage by the web browser (e.g., as a user agent type in an HTTP header associated with a GET request), and the web server may select the appropriate interface based on this embedded identifier, thereby providing an interface appropriately configured for the specific user device in use.

The present system may include, in some embodiments, a datastore configured to store data about users and/or other information. The data store may include various types of data stores, including relational or non-relational databases, document collections, hierarchical key-value pairs, or memory images, for example. Such components may be formed in a single database, document, or the like, or may be stored in separate data structures. In some embodiments, the data store comprises electronic storage media that electronically stores information. The electronic storage media of the data store may include one or both of system storage that is provided integrally (i.e., substantially non-removable) with the system and/or removable storage that is removably connectable to the system via, for example, a port (e.g., a USB port, a firewire port, etc.) or a drive (e.g., a disk drive, etc.). The data store may be (in whole or in part) a separate component within the system, or the data store may be provided (in whole or in part) integrally with one or more other components of the system (e.g., processors, etc.). In some embodiments, the data store may be located in a data center, in a server that is part of the external resources, in a computing device, or in other locations. The data store may include one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), or other electronically readable storage media. The data store may store software algorithms, information determined by the system, information received via the graphical user interface displayed on the computing devices, information received from external resources, or other information accessed by the system to function as described herein.

Figure 1:
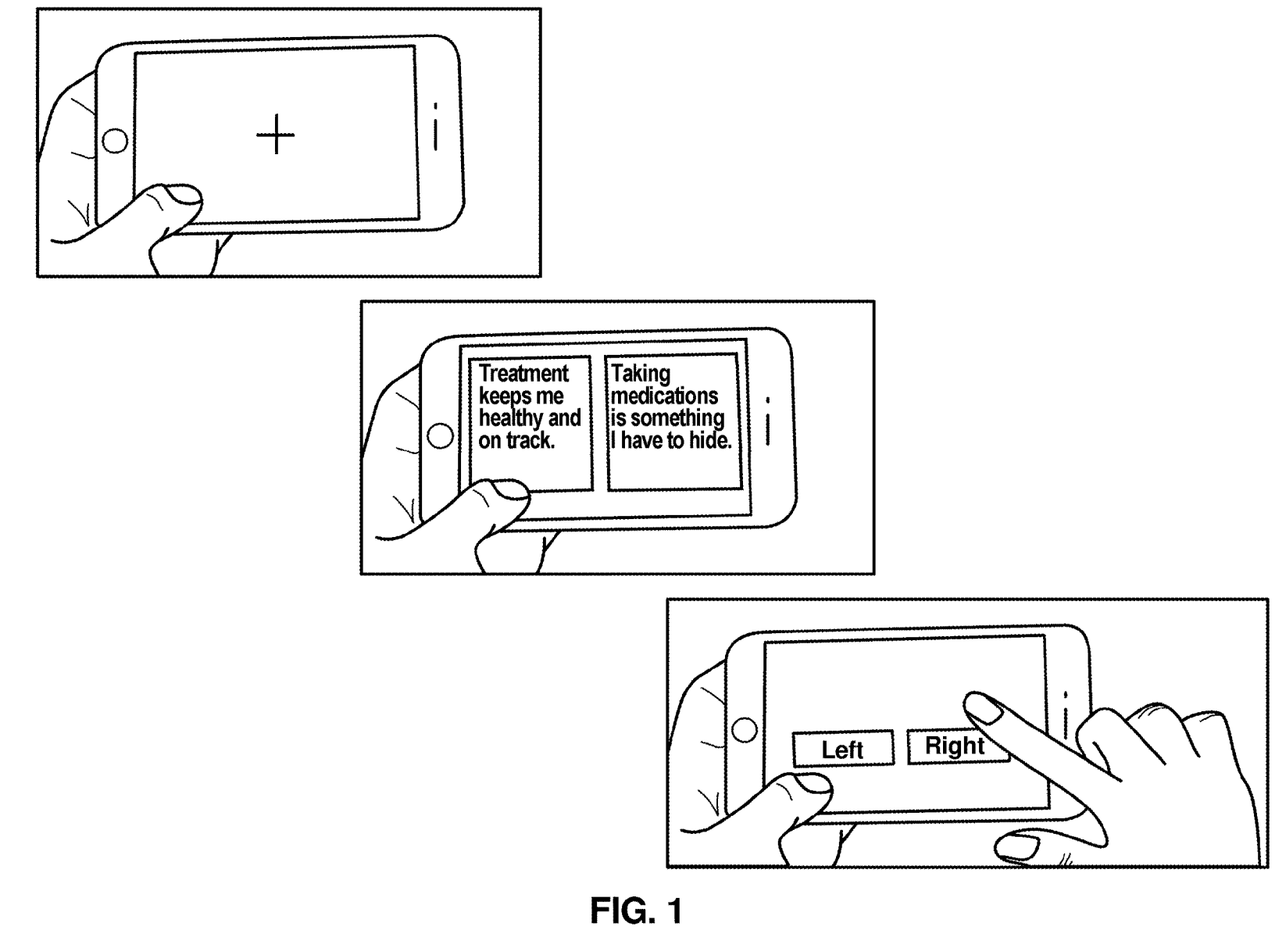
FIG. 1 illustrates individualized attention bias modification delivered via mobile device with stimuli derived from on paired-comparisons techniques and multidimensional scaling analysis (MDS). This figure illustrates an ABM segment that incorporates a patient's own thoughts in the intervention.
Figure 2:
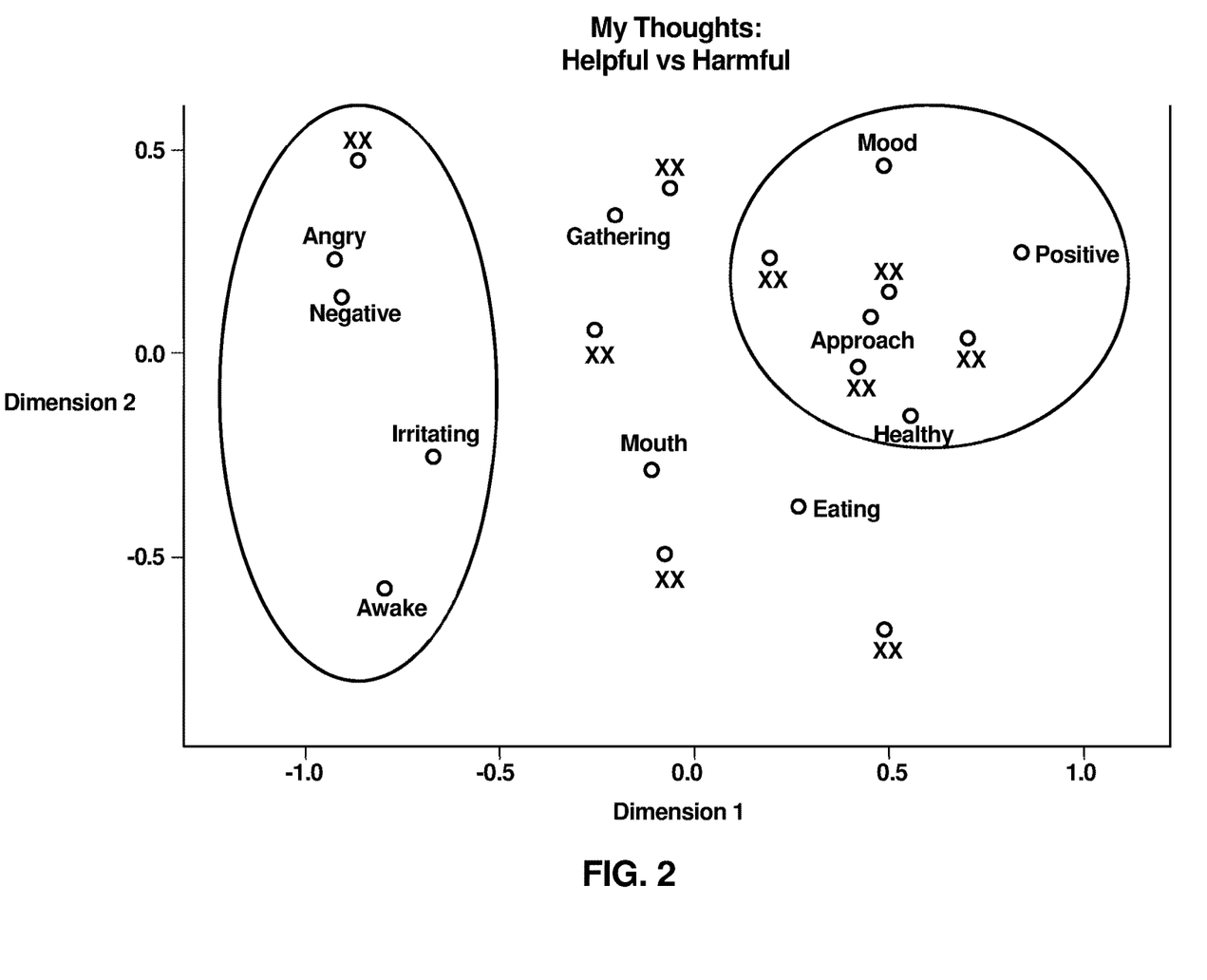
FIG. 2 illustrates individualized cognitive maps could be generated through automated, web-based procedures based on paired-comparisons techniques and multidimensional scaling analysis (MDS). This map depict thoughts and cognitive processes (denoted by one word labels) that trigger opposing treatment-related behavior for a specific client.
Figure 3:
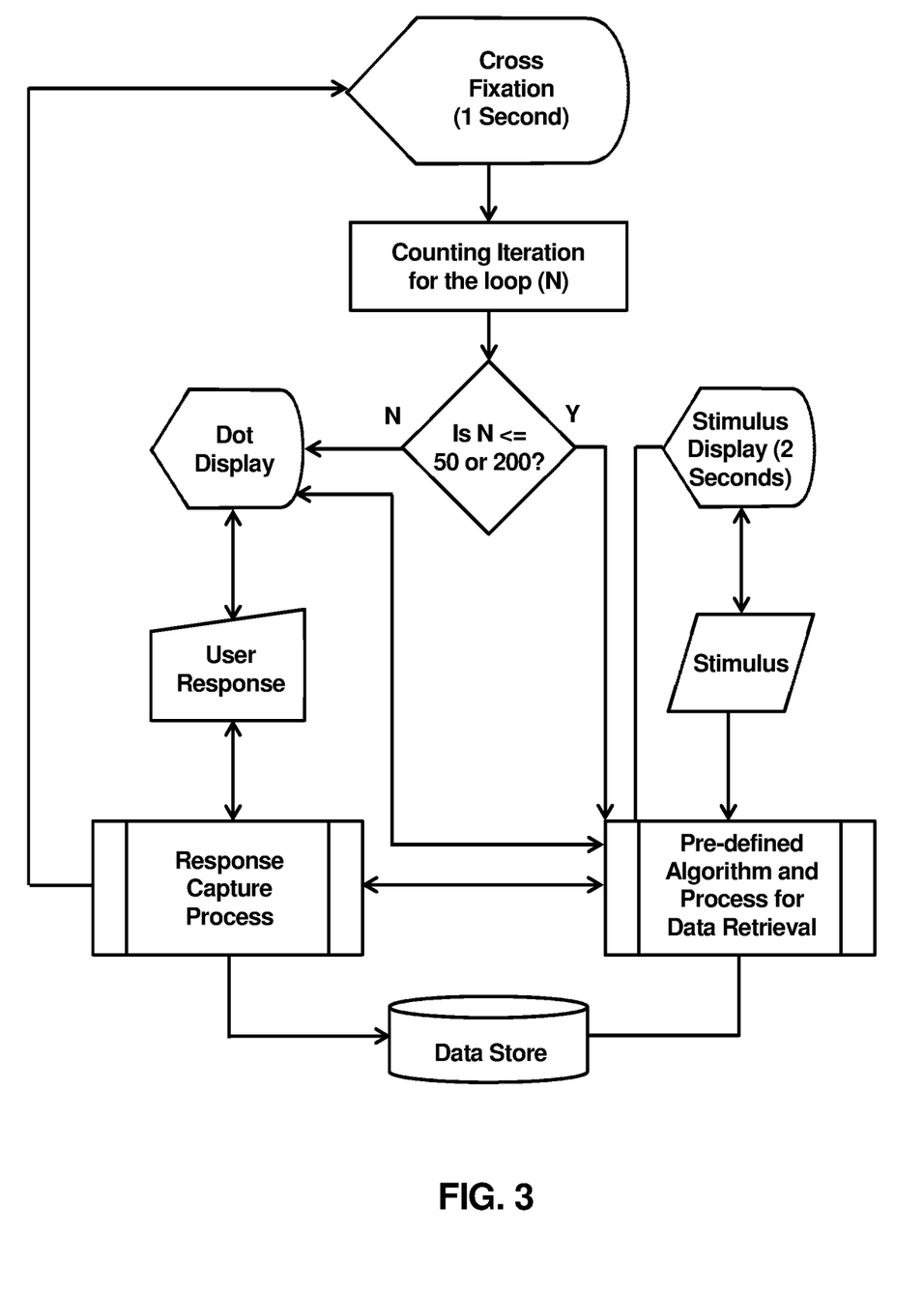
FIG. 3 illustrates a process flow for the idiographic assessment program that generates stimuli for use in attention bias modification (ABM) training interventions, particularly individualized ABM interventions
Figure 4:
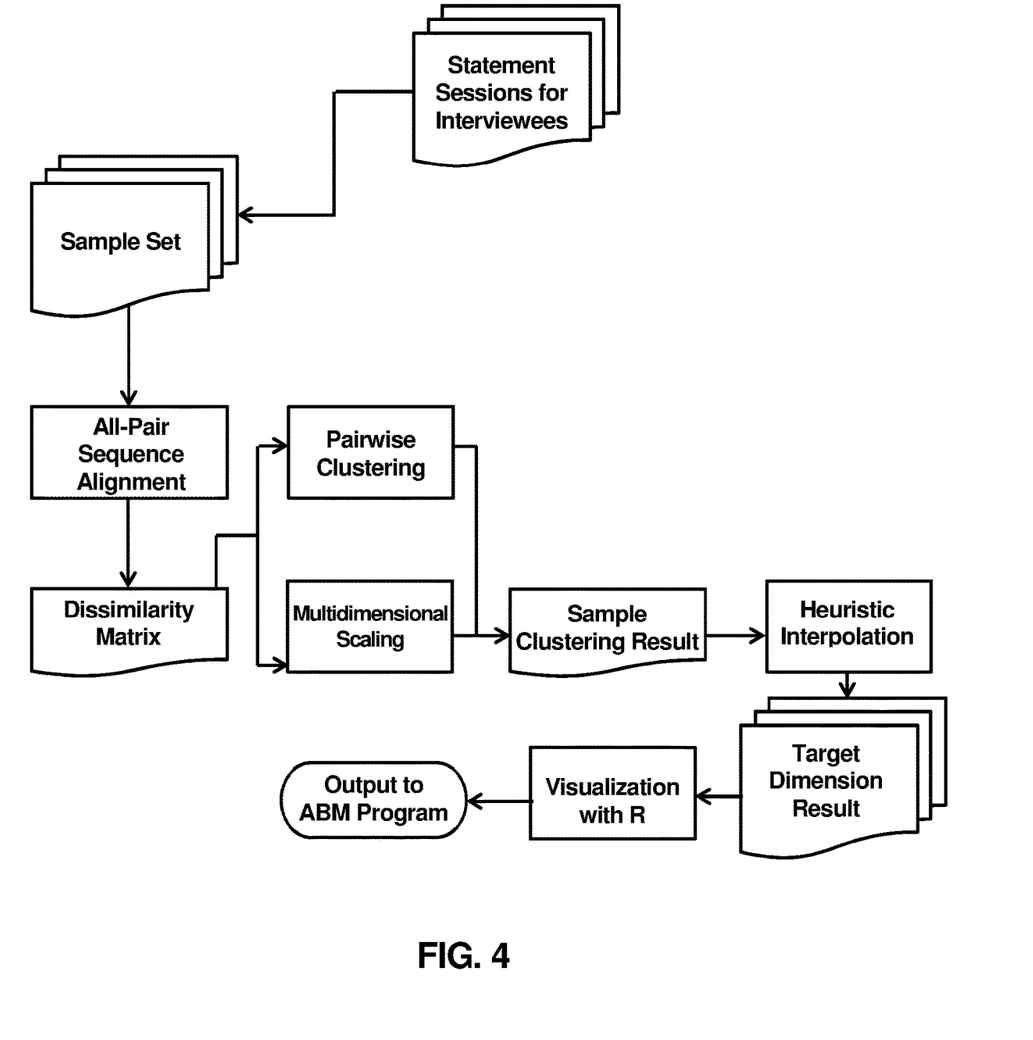
FIG. 4 illustrates a process Flow of the statement session of the input data (paired-comparisons ratings) from a user and transforming the data into a matrix followed by processing of the data in multidimensional scaling analysis.
Figure 5:
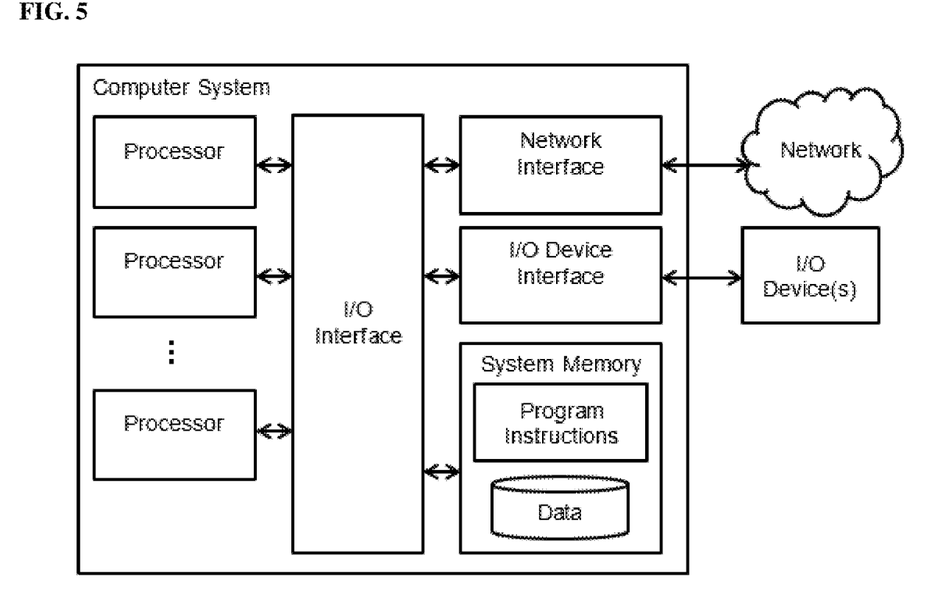
FIG. 5 is a diagram that illustrates an exemplary computing system in accordance with embodiments of the present system.

FIG. 5 is a diagram that illustrates an exemplary computing system in accordance with embodiments of the present system. Various portions of systems and methods described herein, may include or be executed on one or more computer systems the same as or similar to the computing system. Processes, modules, processor components, and/or other components of the system described herein may be executed by one or more processing systems similar to and/or the same as that of the exemplary computing system.

The computing system may include one or more processors coupled to system memory, an input/output I/O device interface, and a network interface via an input/output (I/O)

interface. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of the computing system. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory). The computing system may be a uni-processor system including one processor, or a multi-processor system including any number of suitable processors. Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). The computing system may include a plurality of computing devices (e.g., distributed computer systems) to implement various processing functions.

The I/O device interface may provide an interface for connection of one or more I/O devices to the computer system. I/O devices may include devices that receive input (e.g., from a user) or output information (e.g., to a user). I/O devices may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices may be connected to the computer system through a wired or wireless connection. I/O devices may be connected to the computer system from a remote location. I/O devices located on remote computer system, for example, may be connected to the computer system via a network and network interface.

The network interface may include a network adapter that provides for connection of the computer system to a network. The network interface may may facilitate data exchange between the computer system and other devices connected to the network. The network interface may support wired or wireless communication. The network may include an electronic communication network, such as the Internet, a local area network (LAN), a wide area network (WAN), a cellular communications network, or the like.

The system memory may be configured to store program instructions or data. The program instructions may be executable by a processor (e.g., one or more of processors) to implement one or more embodiments of the present techniques. Instructions may include modules and/or components of computer program instructions for implementing one or more techniques described herein with regard to various processing modules and/or components. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory may include a non-transitory computer readable storage medium that may have program instructions stored thereon that are executable by a computer processor to cause the subject matter and the functional operations described herein. A memory may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times, e.g., a copy may be created by writing program code to a first-in-first-out buffer in a network interface, where some of the instructions are pushed out of the buffer before other portions of the instructions are written to the buffer, with all of the instructions residing in memory on the buffer, just not all at the same time.

An I/O interface may be configured to coordinate I/O traffic between processors, system memory, network interface, other I/O devices, and/or other peripheral devices. The I/O interface may perform protocol, timing, or other data transformations to convert data signals from one component into a format suitable for use by another component. The I/O interface may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of the computer system or multiple computer systems configured to host different portions or instances of embodiments. Multiple computer systems may provide for parallel or sequential processing/execution of one or more portions of the techniques described herein.

Those skilled in the art will appreciate that the computer system described herein is merely illustrative and is not intended to limit the scope of the techniques described herein. The computer system may include any combination of devices or software that may perform or otherwise provide for the performance of the techniques described herein. For example, the computer system may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, a television or device connected to a television (e.g., Apple TV™), or a Global Positioning System (GPS), or the like. The computer system may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 600 may be transmitted to computer system 600 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present invention may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may provided by sending instructions to retrieve that information from a content delivery network.

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to cost constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

What is claimed is:

1. An automated method for clinical assessments and interventions using paired comparisons techniques and multidimensional scaling analysis to enhance user engagement compared to prior methods, determine an individualized assessment for a user, provide the individualized assessment in an immediate and automated manner, and generate attention bias modification trainings that are tailored to the user based on his or her own personally meaningful stimuli, the method comprising:
   determining, with a computer software system, based on responses elicited from the user during an interview, the user's own thoughts, perceptions, and beliefs;
   causing, with the computer software system, generation of stimuli for use in individualized attention bias modification training interventions for the user, the generation of stimuli being part of an idiographic assessment program,
      wherein N-dimensional configurations of the stimuli are generated and displayed automatically to the user; comprise the user's own thoughts, perceptions, and beliefs; and provide data to inform and implement personal clinical interventions specifically for the user;
   receiving, with the computer software system, input information comprising paired comparisons ratings from the user based on the stimuli;
   transforming, with the computer software system, the input information into a data matrix;
   generating, with the computer software system, using multidimensional scaling analysis based on the data matrix, an N-dimensional spatial configuration or mapping that indicates stress values, a least distance value, and R-values for the user; and
   applying the spatial configuration or mapping by:
      (1) cognitively mapping, with the computer software system, the user's thought processes, cognitively mapping comprising causing display of the N-dimensional spatial configuration or mapping, the spatial configuration or mapping comprising an individualized cognitive map determined based on the multidimensional scaling analysis and the paired comparisons ratings, the individualized cognitive map comprising a multidimensional plot depicting thoughts and cognitive processes of the user denoted by indicators at relative locations on the multidimensional plot and corresponding one word labels that trigger opposing treatment-related behavior for the user;
      (2) facilitating motivational interviewing of the user with the computer software system and information from the spatial configuration or mapping, motivational interviewing comprising an individualized assessment that provides immediate information about the user's treatment-related cognitive processes; and
      (3) outputting, with the computer software system, information from the spatial configuration or mapping to an automated attention bias modification program used by the user.

2. The method of claim 1, wherein the stimuli is generated on a smartphone associated with the user.

3. The method of claim 1, wherein the idiographic assessment program operates cross-platform using data from an elicitation task and the paired comparisons techniques.

4. A tangible, non-transitory, machine-readable medium storing instructions that when executed effectuate operations for clinical assessments and interventions using paired comparisons techniques and multidimensional scaling analysis to enhance user engagement, determine an individualized assessment for a user, provide the individualized assessment in an immediate and automated manner, and generate attention bias modification trainings that are tailored to the user based on his or her own personally meaningful stimuli, the operations including:
   determining, with a computer software system, based on responses elicited from the user during an interview, the user's own thoughts, perceptions, and beliefs;
   causing, with computer software system, generation of stimuli for use in individualized attention bias modification training interventions for the user, the generation of stimuli being part of an idiographic assessment program,
      wherein N-dimensional configurations of the stimuli are generated and displayed automatically to the user; comprise the user's own thoughts, perceptions, and beliefs; and provide data to inform and implement personal clinical interventions specifically for the user;
   receiving, with the computer software system, input information comprising paired comparisons ratings from the user;
   transforming, with the computer software system, the input information into a data matrix;

generating, with the computer software system, using multidimensional scaling analysis based on the data matrix, an N-dimensional spatial configuration or mapping that indicates stress values, a least distance value, and R-values for the user; and applying the spatial configuration or mapping by:
(1) cognitively mapping, with the computer software system, the user's thought processes, cognitively mapping comprising causing display of the N-dimensional spatial configuration or mapping, the spatial configuration or mapping comprising an individualized cognitive map determined based on the multidimensional scaling analysis and the paired comparisons ratings, the individualized cognitive map comprising a multidimensional plot depicting thoughts and cognitive processes of the user denoted by indicators at relative locations on the multidimensional plot and corresponding one word labels that trigger opposing treatment-related behavior for the user;
(2) facilitating motivational interviewing of the user with the computer software system and information from the spatial configuration or mapping, motivational interviewing comprising an individualized assessment that provides immediate information about the user's treatment-related cognitive processes; and
(3) outputting, with the computer software system, information from the spatial configuration or mapping to an automated attention bias modification program used by the user.

5. The medium of claim 4, wherein the stimuli is generated on a smartphone associated with the user.

6. The medium of claim 4, wherein the idiographic assessment program operates cross-platform using data from an elicitation task and the paired comparisons techniques.

7. A system comprising one or more processors and memory storing instructions that when executed by the processors cause the processors to effectuate operations for clinical assessments and interventions using paired comparisons techniques and multidimensional scaling analysis to enhance user engagement compared to prior methods, determine an individualized assessment for a user, provide the individualized assessment in an immediate and automated manner, and generate attention bias modification trainings that are tailored to the user based on his or her own personally meaningful stimuli, the operations comprising:

determining, with a computer software system, based on responses elicited from the user during an interview, the user's own thoughts, perceptions, and beliefs;

causing, with a computer software system, generation of stimuli for use in individualized attention bias modification training interventions for the user, the generation of stimuli being part of an idiographic assessment program,
wherein N-dimensional configurations of the stimuli are generated and displayed automatically to the user; comprise the user's own thoughts, perceptions, and beliefs; and provide data to inform and implement personal clinical interventions specifically for the user;

receiving, with the computer software system, input information comprising paired comparisons ratings from the user based on the stimuli;

transforming, with the computer software system, the input information into a data matrix;

generating, with the computer software system, using multidimensional scaling analysis based on the data matrix, an N-dimensional spatial configuration or mapping that indicates stress values, a least distance value, and R-values for the user; and applying the spatial configuration or mapping by:
(1) cognitively mapping, with the computer software system, the user's thought processes, cognitively mapping comprising causing display of the N-dimensional spatial configuration or mapping, the spatial configuration or mapping comprising an individualized cognitive map determined based on the multidimensional scaling analysis and the paired comparisons ratings, the individualized cognitive map comprising a multidimensional plot depicting thoughts and cognitive processes of the user denoted by indicators at relative locations on the multidimensional plot and corresponding one word labels that trigger opposing treatment-related behavior for the user;
(2) facilitating motivational interviewing of the user with the computer software system and information from the spatial configuration or mapping, motivational interviewing comprising an individualized assessment that provides immediate information about the user's treatment-related cognitive processes; and
(3) outputting, with the computer software system, information from the spatial configuration or mapping to an automated attention bias modification program used by the user.

8. The system of claim 7, wherein the stimuli is generated on a smartphone associated with the user.

9. The system of claim 7, wherein the idiographic assessment program operates cross-platform using data from an elicitation task and paired comparisons techniques.

* * * * *